US011071638B2

United States Patent
Xiao et al.

(10) Patent No.: US 11,071,638 B2
(45) Date of Patent: Jul. 27, 2021

(54) IMPLANTATION METHOD OF A STENT SYSTEM

(71) Applicant: LIFETECH SCIENTIFIC (SHENZHEN) CO., LTD, Shenzhen (CN)

(72) Inventors: Benhao Xiao, Shenzhen (CN); Tingbo Ming, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 254 days.

(21) Appl. No.: 16/502,385

(22) Filed: Jul. 3, 2019

(65) Prior Publication Data

US 2021/0000626 A1    Jan. 7, 2021

(51) Int. Cl.
*A61F 2/954* (2013.01)
*A61F 2/966* (2013.01)
*A61M 25/09* (2006.01)

(52) U.S. Cl.
CPC .............. *A61F 2/954* (2013.01); *A61F 2/966* (2013.01); *A61M 25/09041* (2013.01)

(58) Field of Classification Search
CPC .. A61F 2/966; A61F 2/954; A61F 2/07; A61F 2002/061; A61M 25/09041
See application file for complete search history.

(56) References Cited

U.S. PATENT DOCUMENTS

2002/0156518 A1* 10/2002 Tehrani ................... A61F 2/954
                                                                   623/1.11
2005/0010277 A1*  1/2005 Chuter ...................... A61F 2/07
                                                                   623/1.13

* cited by examiner

*Primary Examiner* — Richard G Louis
(74) *Attorney, Agent, or Firm* — Maier & Maier, PLLC

(57) ABSTRACT

An implantation method of a stent system, and the implantation method including implanting a main stent; introducing a catcher; introducing a long sheath and a guiding catheter along a preset guide wire, so as to make the distal end of the long sheath and the distal end of the guiding catheter extend out from the distal end of the inner branch; the distal end of the long sheath and the distal end of the guiding catheter to respectively enter a target branch blood vessel; withdrawing the guiding catheter, and introducing a branch stent delivery along the long sheath to complete the implantation of the branch stent. The method greatly shortens the implantation time of the stent system by simplifying the path of the preset guide wire in the implantation process and fully utilizing the characteristics of the preset guide wire with double soft heads.

18 Claims, 18 Drawing Sheets

IMPLANTATION METHOD OF A STENT SYSTEM

FIELD

The application relates to the field of medical devices, and in particular to an implantation method of a stent system.

BACKGROUND

Thoracic abdominal aortic aneurysm refers to abdominal aortic aneurysm involving the celiac trunk, superior mesenteric artery and renal artery, which is a difficulty in vascular surgical treatment because of its high mortality and difficulty in operation. The current method for treating thoracic abdominal aortic aneurysm mainly includes: 1) Traditional surgery; 2) Hybrid operation; 3) Intra-cavity therapy. Compared with the traditional surgery and hybrid operation, intra-cavity therapy of thoracic abdominal aortic aneurysms has become the focus of interventional therapy with its advantages of less trauma and fewer postoperative complications. And fenestration stent and branch stent are the main methods for intra-cavity therapy of thoracic abdominal aortic aneurysms.

The technique of fenestration stent is to carefully confirm the exact position of each branch artery of thoracic abdominal aorta and obtain accurate anatomical data by fully studying the CT images of a patients before surgery, determine the "fenestration" direction and position in the branch vessel, and customize the stent-type blood vessel to suit the patient's anatomy. During the surgery, accurate positioning of the stent is required, followed by the use of the covered stent. Frequent exchange of guide wires is required to establish the path between the stent and the branch artery, which requires a long surgery time and high technical requirements of surgeon. Meanwhile, the postoperative endoleak is easy to occur due to the short anchoring area of the "fenestration" and the posterior covered stent.

A branch-type stent is different from a fenestration stent in that the branch-type stent is composed of a main body and branches connected with the main body as part of the stent, and is released with the main body and the branches clearly positioned, further the distal end of the branch-type stent can be connected with a self-expanding covered stent in a reconnecting mode, and the anchoring areas of the branch-type stent and the reconnected covered stent are longer, making the incidence of postoperative endoleak lower than that of the fenestration stent. However, when the branch-type stent is followed by the covered stent, the guide wire needs to pass through the branch of the stent and then be selected into the branch blood vessel, so as to establish the path between the stent and the branch artery. For complicated twisted aneurysms, the difficulty that the guide wire passes through the branch of the stent is great, thereby, currently the preset guide wire technology being widely applied in the branch-type stent to reduce the difficulty of guiding catheter entering the branch artery. However, at present, frequent exchange of guide wires is required during the implantation of the stent with preset guide wire, or the preset guide wire as a whole needs to be used throughout the artery, resulting in a long implantation time.

Therefore, it is necessary to provide a stent implantation method which can simplify the implantation process and shorten the implantation time.

SUMMARY

Exemplary embodiments of the present application provides an implantation method of a stent system, which includes a main stent, a branch stent and a preset guide wire, where the main stent includes an inner branch, the preset guide wire penetrates through the inner branch, and the implantation method of the stent system includes the following steps:

implanting the main stent through a lower limb artery;

introducing a catcher system through an upper limb artery, where the catcher system includes a catcher, using the catcher to catch the preset guide wire, and withdrawing the catcher to enable the upper end of the preset guide wire to be exposed out of the upper limb artery;

guiding a long sheath and a guiding catheter along the preset guide wire through the upper limb artery, where the long sheath and the guide catheter are respectively provided with a proximal end and a distal end which are opposite, so as to make the distal end of the long sheath and the distal end of the guiding catheter extend out from the distal end of the inner branch;

withdrawing the preset guide wire from the lower limb artery;

guiding a vascular selection guide wire along the guiding catheter through the upper limb artery, and operating the vascular selection guide wire to enable the lower end of the vascular selection guide wire to enter a target branch blood vessel;

operating the guiding catheter and the long sheath to enable the distal end of the long sheath and the distal end of the guiding catheter to enter the target branch blood vessel along the vascular selection guide wire; and withdrawing the guiding catheter from the upper limb artery and guiding a branch stent delivery through the upper limb artery along the long sheath to complete the implantation of the branch stent.

Exemplary embodiments of the present application further provide an implantation method of another stent system, where the stent system includes a main body stent, a branch stent and a preset guide wire, the main body stent includes an inner branch, the preset guide wire penetrates through the inner branch, and the implantation method of the stent system includes the following steps:

implanting the main stent through a lower limb artery;

introducing a catcher system through an upper limb artery, where the catcher system includes a catcher, using the catcher to catch the preset guide wire, and withdrawing the catcher to enable the upper end of the preset guide wire to be exposed out of the upper limb artery;

guiding a long sheath and a guiding catheter along the preset guide wire through the upper limb artery, where the long sheath and the guiding catheter are respectively provided with a proximal end and a distal end which are opposite, so as to make the distal end of the long sheath and the distal end of the guiding catheter extend out from the distal end of the inner branch; operating the upper end of the preset guide wire to enable the lower end of the preset guide wire to enter a target branch blood vessel;

operating the guiding catheter and the long sheath to enable the distal end of the long sheath and the distal end of the guiding catheter to enter the target branch blood vessel along the preset guide wire; and withdrawing the guiding catheter through the upper limb artery, and guiding a branch stent delivery along the long sheath through the upper limb artery to complete the implantation of the branch stent.

Exemplary embodiments of the present application further provide an implantation method of another stent system, where the stent system includes a main body stent, a branch stent and a preset guide wire, the main body stent includes an inner branch, the preset guide wire penetrates through the inner branch, and the implantation method of the stent system includes the following steps:

implanting the main stent through a lower limb artery;

introducing a catcher system through an upper limb artery, where the catcher system includes a catcher and a catcher catheter, the catcher is used for catching the preset guide wire and pulling down the preset guide wire through a femoral artery, and pushing the catcher system downwards to enable the lower end of the catcher catheter to extend from the distal end of the inner branch along the preset guide wire;

withdrawing the preset guide wire through the lower limb artery, and guiding a vascular selection guide wire through the upper limb artery along the catcher catheter;

withdrawing the catcher catheter, introducing a long sheath and a guiding catheter along the vascular selection guide wire via the upper limb artery, where the long sheath and the guiding catheter are respectively provided with a proximal end and a distal end which are opposite, so as to make the distal end of the long sheath and the distal end of the guiding catheter extend out from the distal end of the inner branch;

operating the vascular selection guide wire to enable the lower end of the vascular selection guide wire to enter a target branch blood vessel;

operating the long sheath and the guiding catheter to enable the distal end of the long sheath and the distal end of the guiding catheter to enter the target branch blood vessel along the vascular selection guide wire; and withdrawing the guiding catheter from the upper limb artery and guiding a branch stent delivery through the upper limb artery along the long sheath to complete the implantation of the branch stent.

According to the implantation method of the stent system provided by exemplary embodiments of the present application, the path of the preset guide wire in the implantation process is simplified, and the characteristics of the preset guide wire with double soft heads are fully utilized, thereby greatly shortening the implantation time of the stent system.

DETAILED DESCRIPTION OF THE EMBODIMENTS

The technical scheme and beneficial effects of the present application will be better understood with the following further detailed description and the accompanying drawings.

The preliminary definition of some positional relationships is depicted below for ease of description. For a delivery, the end near an operator is defined as the "proximal end" and the end away from the operator is defined as the "distal end", for example, when operating the delivery, the end relatively near the operator is the proximal end of the delivery and the end away from the operator is the distal end of the delivery. For an implanted object, such as a stent, the blood inflow end is defined as "proximal end" and the blood outflow end is "distal end". For objects requiring repeated operation, such as guide wires, one end close to the foot of a human body is defined as "lower end" and one end close to the head of a human body is defined as "upper end".

Figure 1:
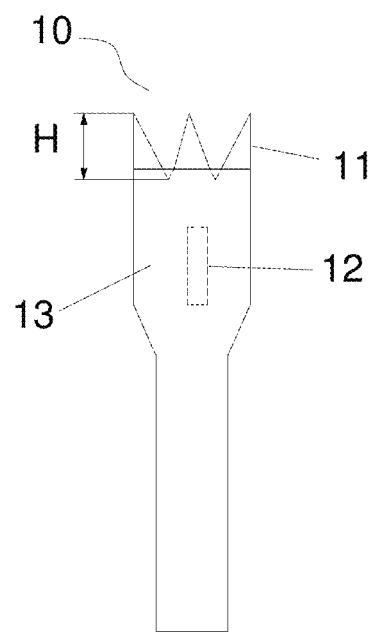
FIG. 1 is a schematic diagram showing a structure of a main stent in a stent system according to the present application.
Figure 2:
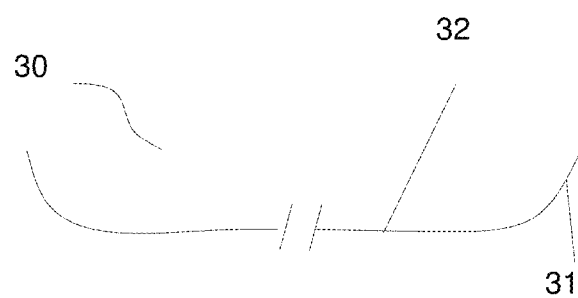
FIG. 2 is a schematic diagram showing a structure of a preset guide wire in a stent system according to the present application.

Referring to FIG. 1 and FIG. 2, the stent system according to the present application includes a main stent 10, a branch stent 20 (not shown in FIG. 1), and a preset guide wire 30. The preset guide wire 30 is partially provided inside the main stent 10, and the branch stent 20 is used in coordination with the main stent 10. The main stent 10 includes a covered section 13, a bare stent 11, and an inner branch 12. The bare stent 11 is provided at the proximal end of the covered section 13; the inner branch 12 is provided inside the covered section 13, and the proximal opening of the inner branch 12 is connected internally with the covered section 13, and the distal opening of the inner branch 12 is connected externally with the covered section 13. It should be understood that the number of inner branch 12 may be set as many as practical.

The preset guide wire 30 includes two tips 31 and a body 32 connecting the two tips, where the tips 31 are J-shaped soft head, that is, the hardness of the tips 31 is lower than that of the body 32, so as to make the preset guide wire 30 to be used as a vascular selection guide wire and/or a delivery access guide wire. It will be appreciated that in some embodiments, when the preset guide wire 30 is used as both a vascular selection guide wire and a delivery access guide wire, the hardness of the tips 31 is set according to the hardness requirements of the vascular selection guide wire described below, while the hardness of the body 32 is set according to the hardness requirements of the delivery access guide wire described below. In the field of interventional medical treatment, a vascular selection guide wire is used for operating and entering a target blood vessel and is mostly a soft guide wire, with the inner core of nickel-titanium alloy and the hardness of about 20 HRC; while the delivery access guide wire is mostly a hard guide wire and used for guiding the delivery to a target position, with the inner cores of mostly hard stainless steel or super-hard stainless steel, and the hardness of about 36 HRC.

Figure 3:
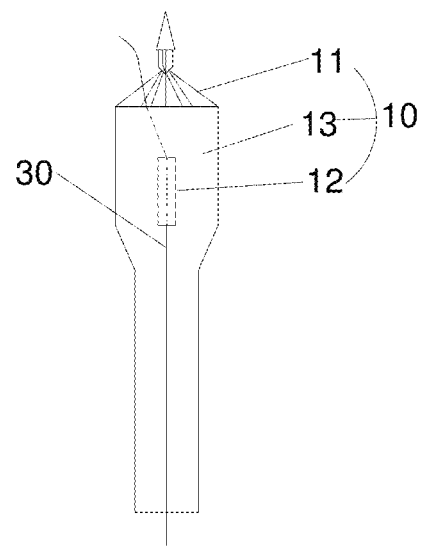
FIG. 3 is a schematic diagram showing the structure of the main stent shown in FIG. 1 and the preset guide wire shown in FIG. 2 when assembled.

In the stent system according to the present application, the positional relationship of the main stent 10 and the preset guide wire 30 is shown in FIG. 3. The upper end of the preset guide wire 30 penetrates from the distal opening of the inner branch 12 and passes through the proximal opening of the inner branch 12 to the inside of the covered section 13, and further passes between the bare stent 11. In order to prevent the preset guide wire 30 from being pressed to affect subsequent catching after the bare stent 11 is unfolded, for example, the upper end of the preset guide wire 30 passes between two adjacent proximal wave peaks in the bare stent 11. Further, the relationship between the length L of the J-shaped tips 31 and the wave height H of the bare stent 11 is L=(1.2–3)*H in order to simultaneously ensure that the preset guide wire can be successfully caught by a catcher without affecting the pushing of the stent due to the excessively long J-shaped tips 31. It will be appreciated that when a number of inner branches are provided on a main stent, one preset guide wire may be provided for each inner branch.

Figure 4:
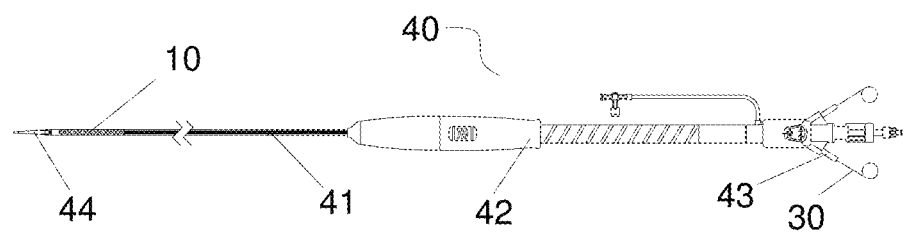
FIG. 4 is a schematic diagram showing a structure of a main stent delivery.

A delivery for a main stent provided by the present application is shown in FIG. 4. The delivery 40 includes a handle 42, a sheath tube 41, a tip head 44, a locking mechanism 43 and an inner core (not signed). The proximal end of the sheath tube 41 is connected to the handle 42 by which the sheath tube 41 can be withdrawn. The inner core is inserted into the sheath tube 41 to support the stent. The proximal end of the inner core is connected to the handle 42 and the distal end of the inner core is configured with the tip head 44 for guiding the delivery system. Operating the different control portions of the handle 42 separately allow the sheath tube 41 and the inner core to be withdrawn separately, thereby achieving a stepwise release of a stent. There are a variety of handles available to achieve a stepwise release of a stent, and the detailed construction of the handle 42 is not depicted herein. The proximal part of the handle 42 is configured with a preset guide wire locking mechanism 43, which can limit the axial movement of the preset guide wire 30 after being locked. The main stent 10 is compressively bound to the distal end of the sheath tube 41, and the bare stent 11 is connected to the proximal end of the tip head. One part of the preset guide wire 30 is compressed inside the sheath tube 41 along with the main stent 10 and the other part extends into the handle 42 and penetrates out through the proximal end of the locking mechanism 43 which is in a locked state. An operator can operate a part of the preset guide wire 30 exposed at the proximal end of the locking mechanism 43 by unlocking the locking mechanism 43, thereby realizing the movement of the preset guide wire 30 inside the body.

Figure 5:
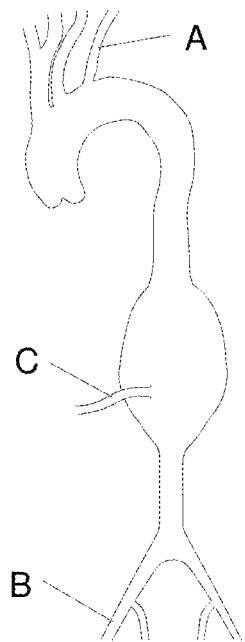
FIG. 5 is a schematic illustration of the vascular structure of abdominal aortic aneurysm.

Hereinafter, an implantation method of the stent system of the present application will be described in detail with an example of reconstructing the paths for thoracic abdominal aorta and branch artery as shown in FIG. 5. In these examples, A is the left clavicular artery in the upper limb artery, B is the right femoral artery in the lower limb artery, and C is the superior mesenteric artery in the branch artery.

Figure 6A:
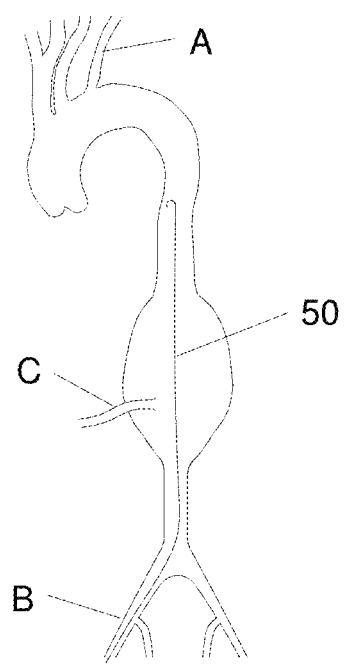
FIG. 6A shows a diagram outlining an implantation method of a stent system according to a first exemplary embodiment of the present application.
Figure 6B:
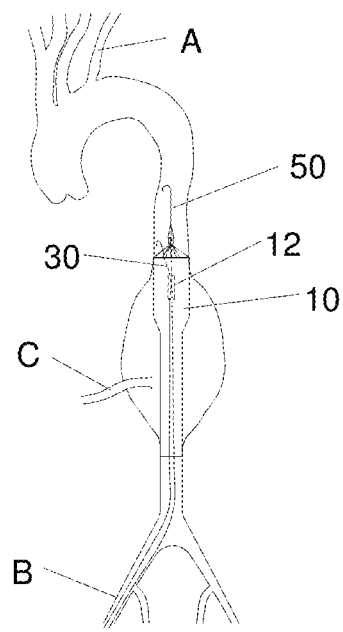
FIG. 6B shows a diagram outlining an implantation method of a stent system according to a first embodiment of the present application.
Figure 6C:
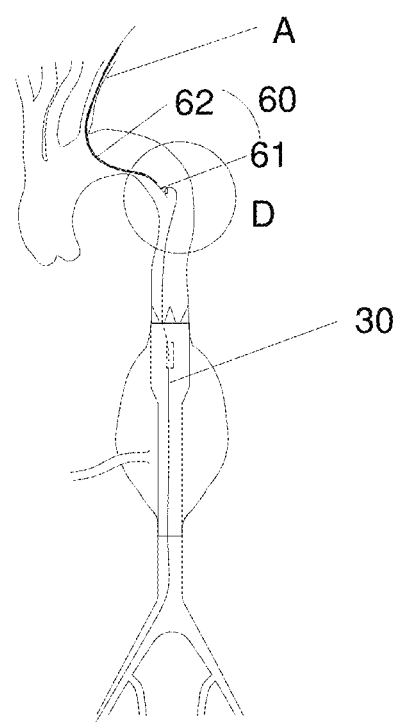
FIG. 6C shows a diagram outlining an implantation method of a stent system according to a first embodiment of the present application.
Figure 6D:
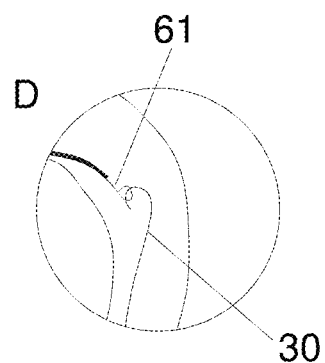
FIG. 6D shows a partially enlarged drawing outlining an implantation method of a stent system according to a first embodiment of the present application.
Figure 6E:
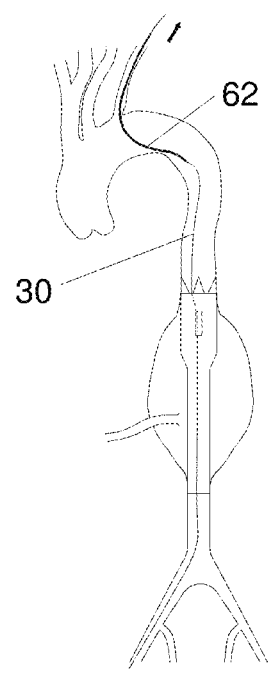
FIG. 6E shows a diagram outlining an implantation method of a stent system according to a first embodiment of the present application.
Figure 6F:
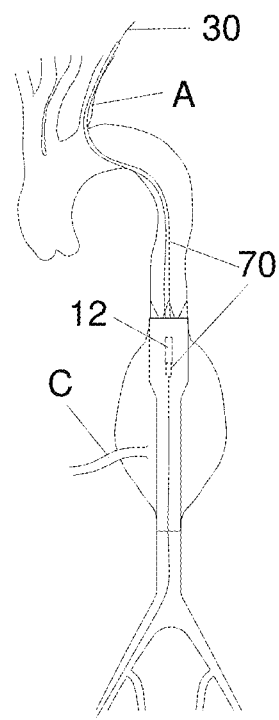
FIG. 6F shows a diagram outlining an implantation method of a stent system according to a first embodiment of the present application.
Figure 6G:
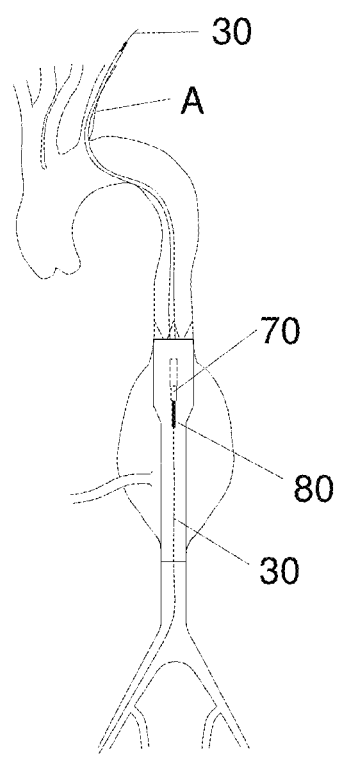
FIG. 6G shows a diagram outlining an implantation method of a stent system according to a first embodiment of the present application.
Figure 6H:
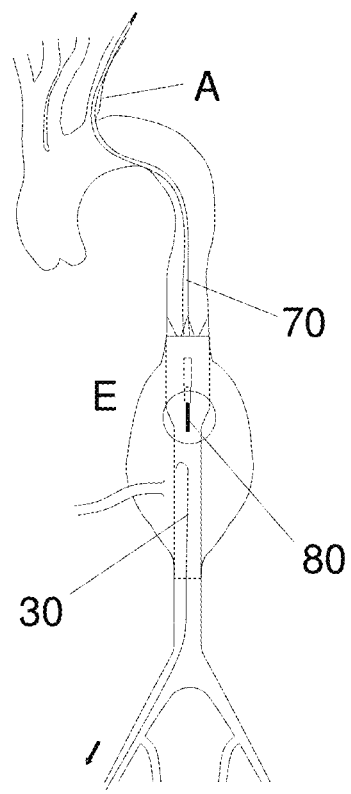
FIG. 6H shows a diagram outlining an implantation method of a stent system according to a first embodiment of the present application.
Figure 6I:
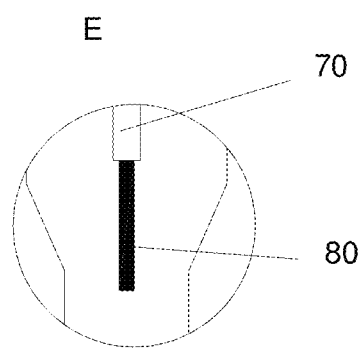
FIG. 6I shows a partially enlarged drawing outlining an implantation method of a stent system according to a first embodiment of the present application.
Figure 6J:
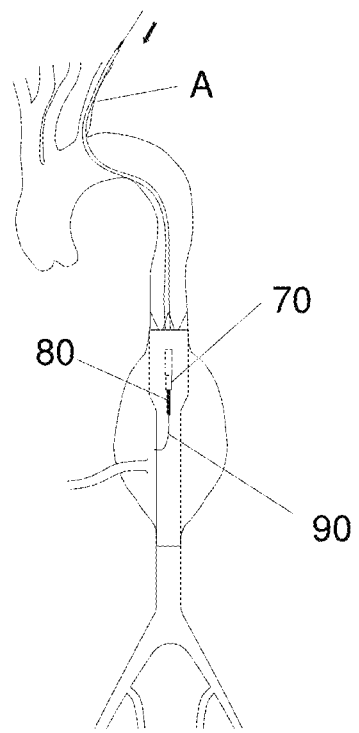
FIG. 6J shows a diagram outlining an implantation method of a stent system according to a first embodiment of the present application.
Figure 6K:
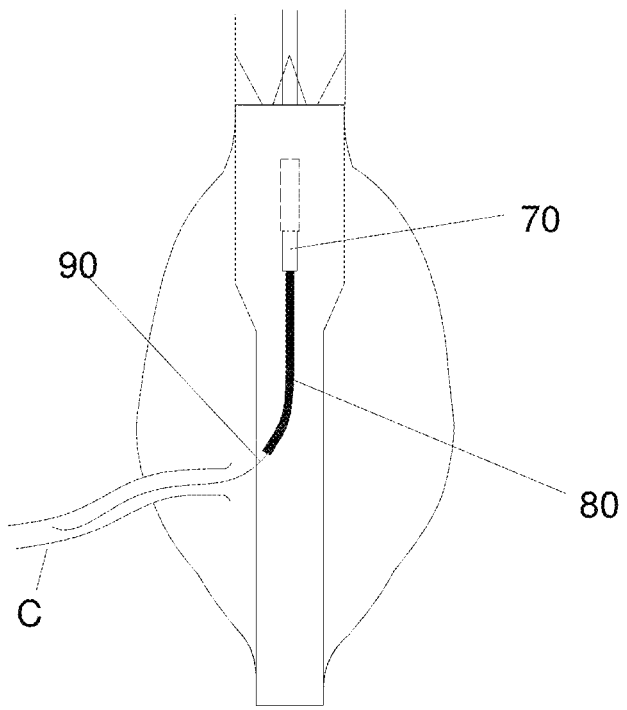
FIG. 6K shows a partially enlarged drawing outlining an implantation method of a stent system according to a first embodiment of the present application.
Figure 6L:
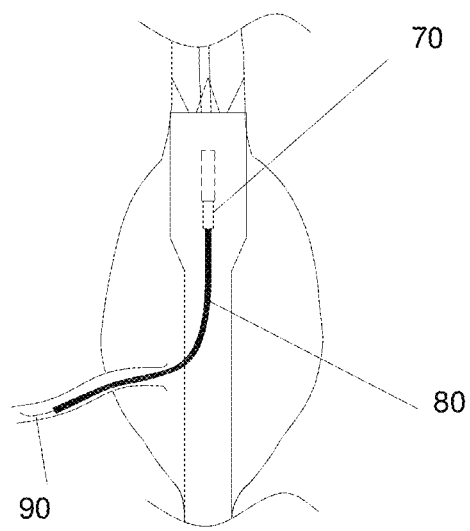
FIG. 6L shows a partially enlarged drawing outlining an implantation method of a stent system according to a first embodiment of the present application.
Figure 6M:
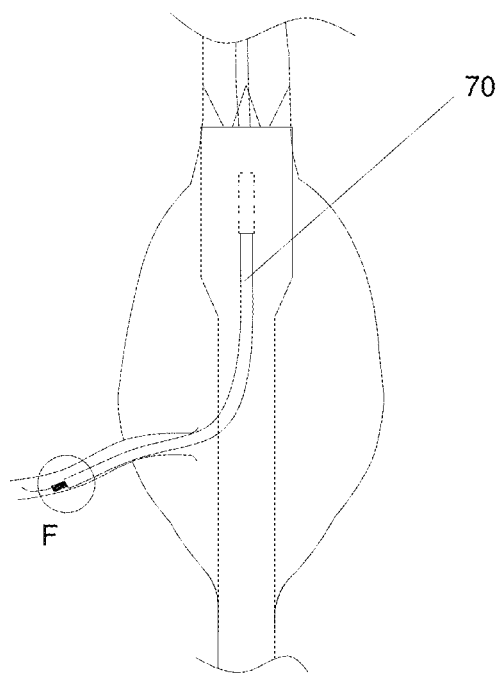
FIG. 6M shows a partially enlarged drawing outlining an implantation method of a stent system according to a first embodiment of the present application.
Figure 6N:
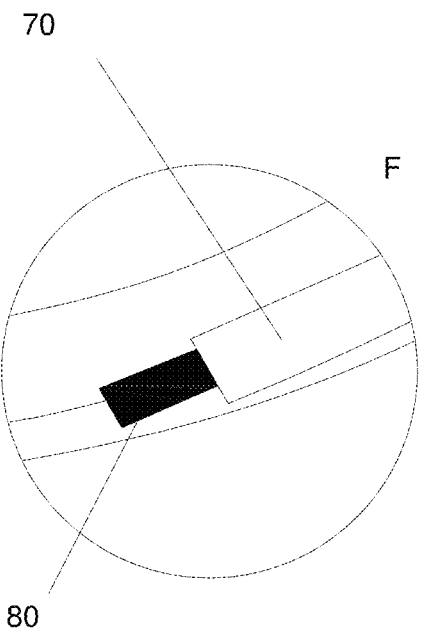
FIG. 6N shows a partially enlarged drawing outlining an implantation method of a stent system according to a first embodiment of the present application.
Figure 6O:
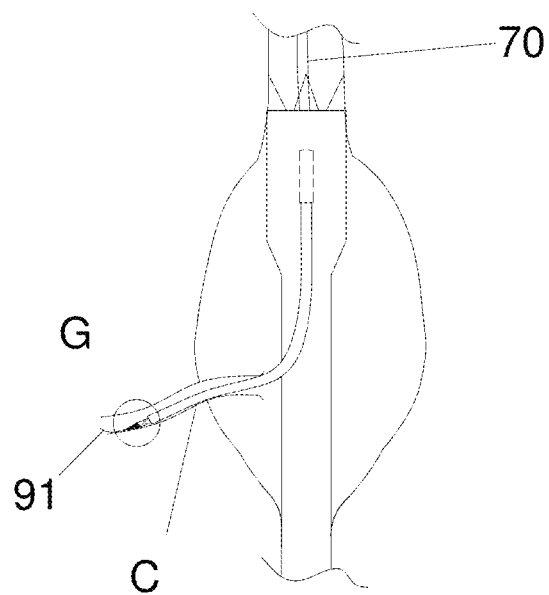
FIG. 6O shows a partially enlarged drawing outlining an implantation method of a stent system according to a first embodiment of the present application.
Figure 6P:
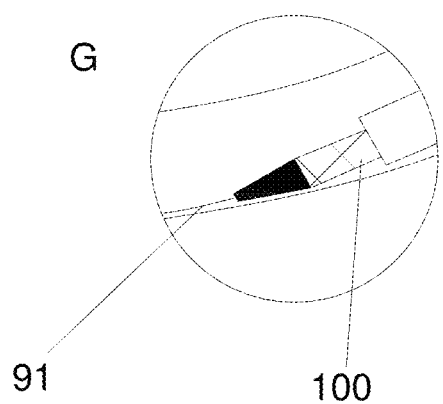
FIG. 6P shows a partially enlarged drawing outlining an implantation method of a stent system according to a first embodiment of the present application.
Figure 6Q:
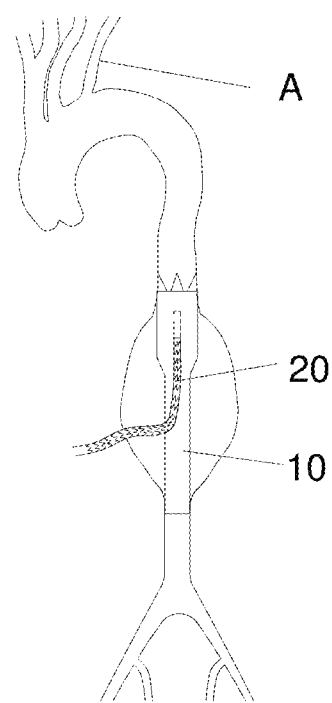
FIG. 6Q shows a diagram outlining an implantation method of a stent system according to a first embodiment of the present application.
Figure 7A:
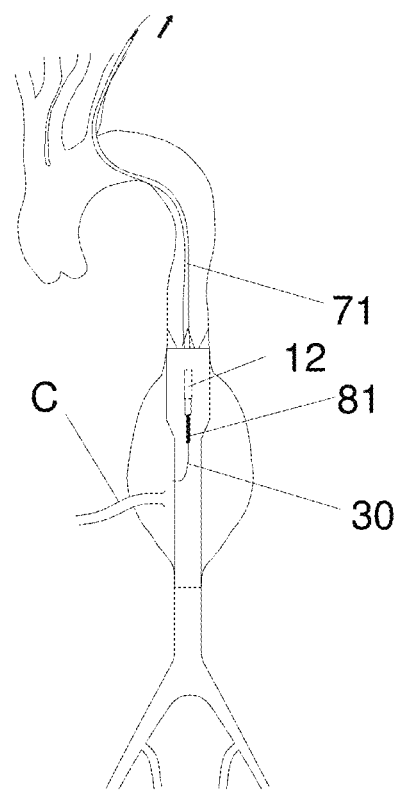
FIG. 7A shows a diagram outlining an implantation method of a stent system according to a second exemplary embodiment of the present application.
Figure 7B:
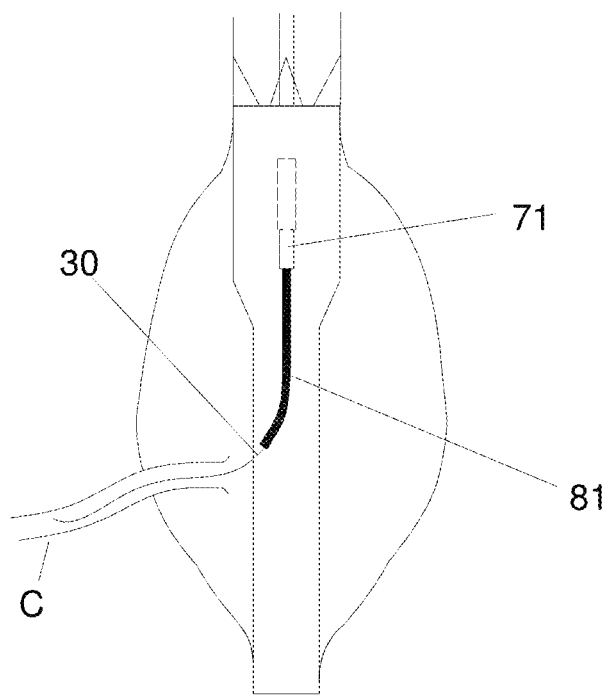
FIG. 7B shows a diagram outlining an implantation method of a stent system according to a second exemplary embodiment of the present application.
Figure 7C:
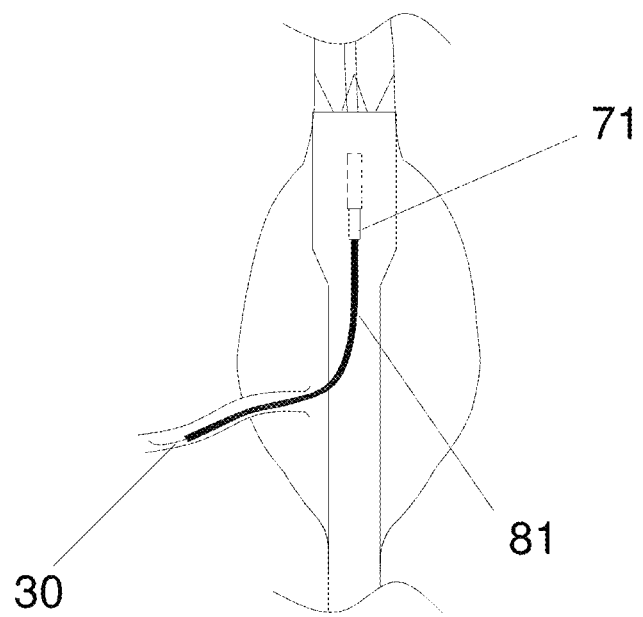
FIG. 7C shows a partially enlarged drawing outlining an implantation method of a stent system according to a second exemplary embodiment of the present application.
Figure 7D:
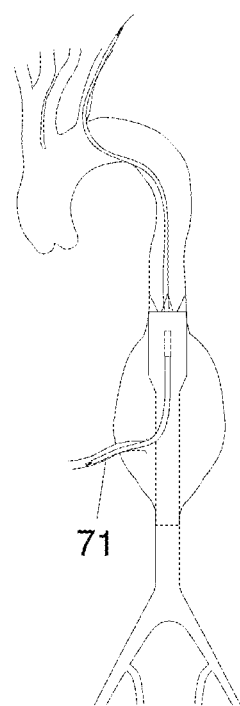
FIG. 7D shows a diagram outlining an implantation method of a stent system according to a second exemplary embodiment of the present application.

In a first exemplary embodiment, FIG. 6A to FIG. 6Q illustrate an implantation method of a stent system, including the steps of:

S10. implanting a main stent through a lower limb artery;

S20. introducing a catcher system through an upper limb artery, where the catcher system includes a catcher, using the catcher to catch the preset guide wire and withdrawing the catcher to enable the upper end of the preset guide wire to be exposed out of the upper limb artery;

S30. introducing a guiding catheter and a long sheath along the preset guide wire through the upper limb artery, where the long sheath and the guiding catheter are respectively provided with a proximal end and a distal end which are opposite, so as to make the distal end of the guiding catheter and the distal end of the long sheath extend out from the distal end of the inner branch;

S40. withdrawing the preset guide wire from the lower limb artery; introducing a vascular selection guide wire along the guiding catheter through the upper limb artery, and operating the vascular selection guide wire to enable the lower end thereof to enter a target branch blood vessel; operating the long sheath and the guiding catheter to enable the distal end of the long sheath and the distal end of the guiding catheter to enter the target branch blood vessel along the vascular selection guide wire;

S50. withdrawing the guiding catheter from the upper limb artery, and introducing a branch stent delivery through the upper limb artery along the long sheath to complete the implantation of a branch stent.

Specifically, as shown in FIG. 6A and FIG. 6B, the step of S10 includes: S101, exposing the positions of the right femoral artery B and the left clavicular artery A of a patient, puncturing a target blood vessel by standard Seldinger method, and inserting a vascular sheath (not shown) respectively at the position of the left clavicular artery A and the position of the right femoral artery B for later use; S102, introducing a vascular selection guide wire (not shown) into the vascular sheath (not shown) at the right femoral artery B, enabling the vascular selection guide wire to reach a designated position of the descending aorta (i.e. the upper end of the aneurysm lesion), introducing a guiding catheter (not shown) along the vascular selection guide wire, withdrawing the vascular selection guide wire, exchanging a delivery access guide wire 50, and withdrawing the guiding catheter, i.e. the state as shown in FIG. 6A; S103, introducing the main stent delivery 40 along the delivery access guide wire 50 at the opening of the right femoral artery B, operating the handle 42 to withdraw the sheath tube 41 towards the proximal end when the main stent 10 compressed in the sheath tube 41 is positioned at the target release position, and expanding the covered section of the main stent 10 to be attached to the inner wall of the blood vessel, namely the state as shown in FIG. 6B; S104, operating the handle 42 to withdraw the inner core, so as to release the bare stent 11 from the proximal end of the tip head 44, unlocking the locking mechanism 43, withdrawing the delivery 40 integrally to enable the distal end thereof to be positioned at the distal end of the main stent 10 and the distal opening of the inner branch 12 to be positioned at the upper end of the superior mesenteric artery C, thereby releasing the main stent 10, making the position of the delivery access guide wire 50 immobile; and S105, operating the lower end of the preset guide wire 30 to push the upper end of the preset guide wire 30 to the descending aorta section, namely the upper end of the aneurysm lesion. The delivery access guide wire 50 is not depicted in the figures following for ease of viewing, which will be withdrawn immediately following the subsequent preset guide wire 30.

Referring to FIG. 6C to FIG. 6E, the step of S20 includes: S201, introducing a catching system 60 with the left clavicular artery A as an access path, where the catching system 60 includes a catcher catheter 62 and a catcher 61 crossing through the catcher catheter 62; S202, continuously pushing the catcher system 60 towards the lower end to enable the distal end thereof to be close to the upper end of the preset guide wire 30, and operating the catcher system 60 to catch the preset guide wire 30 as shown in FIG. 6C; S203, withdrawing the catcher 61 so as to make the upper end of the preset guide wire 30 received into the catcher catheter 62 along with the catcher 61, withdrawing the catcher system 60, thereby exposing the upper end of the preset guide wire 30 outside of the left clavicular artery A, and withdrawing the catcher system 60; S204, fixing the lower end of the preset guide wire 30 by the locking mechanism 43 on the delivery 40, and fixing the upper end of the preset guide wire 30 in a clamping manner, thereby making the preset guide wire 30 keep a certain tension.

Referring to FIG. 6F to FIG. 6I, the step of S30 includes: S301, introducing a long sheath 70 from the left clavicular artery A along the preset guide wire 30 into the blood vessel until the distal end of the long sheath 70 passes through the distal opening of the inner branch 12, as shown in FIG. 6F; S302, introducing a guiding catheter 80 into the long sheath 70 along the upper end of the preset guide wire 30, and continuing to push towards the lower end until the distal end of the guiding catheter 80 penetrates through the distal end of the long sheath 70, as shown in FIG. 6G; S303, loosening the upper end of the preset guide wire 30, unlocking the locking mechanism 43, operating the lower end of the preset guide wire 30 to withdraw the preset guide wire 30 from the opening of the femoral artery B, and then withdrawing the delivery access guide wire 50 and the main stent delivery 40, as shown in FIG. 6H.

Referring to FIG. 6J to FIG. 6N, the step of S40 includes: S405, withdrawing the preset guide wire 30 from the lower limb artery, completely withdrawing the preset guide wire 30, exchanging a vascular selection guide wire 90, and introducing the vascular selection guide wire 90 along the guiding catheter 80 through the upper limb artery; S406, pushing the guiding catheter 80 downwards until the distal end thereof is positioned at the opening of the branch blood vessel, pushing the vascular selection guide wire 90 downwards along the guiding catheter 80 from the left clavicular artery A, so as to make the lower end of the vascular selection guide wire 90 enter the superior mesenteric artery C, as shown in FIG. 6J and FIG. 6K; S407, keeping the long sheath 70 and the vascular selection guide wire 90 immobile, pushing the guiding catheter 80 downwards along the vascular selection guide wire 90 to enable the lower end of the guiding catheter 80 to enter the superior mesenteric artery C as shown in FIG. 6L; S408, keeping the vascular selection guide wire and the guiding catheter 80 immobile, and pushing the long sheath 70 downwards along the guiding catheter 80 to enable the lower end of the long sheath 70 to enter the superior mesenteric artery C, as shown in FIG. 6M. It will be appreciated that the long sheath need not be operated entering into the branch vessel at S408 when the branch stent delivery includes an outer sheath.

At S30 and S40, both the long sheath and the guiding catheter are used at the same time, with the long sheath 70 having a good bending resistance, thereby establishing a good conveying path for the stent delivery within a bent blood vessel; and the better directivity and adjustability of the guiding catheter 80 making a branched path be better established.

Referring to FIG. 6O to FIG. 6Q, the step of S50 includes: S501, exchanging a delivery access guide wire 91, withdrawing the vascular selection guide wire 90 from the left clavicular artery A, and pushing the delivery access guide wire 91 downwards from the left clavicular artery A along the guiding catheter 80; S502, withdrawing the guiding catheter 80 from the upper limb artery, pushing a branch stent delivery 100 downwards from the left clavicular artery A along the delivery access guide wire 91 to enable the distal end of the branch stent delivery 100 to enter the superior mesenteric artery C through the long sheath 70; S503, withdrawing the long sheath 70 to make the branch stent not covered by the long sheath 70 and the branch stent be attached to the blood vessel wall after being released, and then operating the branch stent delivery 100 to release the branch stent 20, so as to withdraw the branch stent delivery 100 and the long sheath 70 after the branch stent 20 is completely released, and the implantation of the stent system is completed, as shown in FIG. 6Q.

It will be appreciated that in other embodiments, when the support performance requirement for the access guide wire is relatively low, the vascular selection guide wire may be directly used as a delivery access guide wire without exchanging the delivery access guide wire at S502.

In the embodiment, the long sheath and the guiding catheter are guided to enter the inner branch of the main stent through the preset guide wire, thereby facilitating the establishment of a subsequent branch path and the implantation of the branch stent, shortening the stent implantation time and improving the accuracy of the branch conveying.

The implantation method of the stent system according to a second exemplary embodiment is substantially the same as that of the stent system in the first exemplary embodiment, including the following steps:

S10. implanting a main stent through a lower limb artery;

S20. introducing a catcher system through an upper limb artery, where the catcher system includes a catcher, using the catcher to catch the preset guide wire and withdrawing the catcher to enable the upper end of the preset guide wire to be exposed out of the upper limb artery;

S30. guiding a long sheath and a guiding catheter along the preset guide wire through the upper limb artery, where the long sheath and the guiding catheter are respectively provided with a proximal end and a distal end which are opposite, so as to make the distal end of the long sheath and the distal end of the guiding catheter extend out from the distal end of the inner branch;

S40. operating the upper end of the preset guide wire to enable the lower end of the preset guide wire to enter a target branch blood vessel; operating the long sheath and the guiding catheter to enable the distal end of the guiding catheter and the distal end of the long sheath to enter the target branch blood vessel along the preset guide wire;

S50. withdrawing the guiding catheter from the upper limb artery, and introducing a branch stent delivery through the upper limb artery along the long sheath to complete the implantation of the branch stent.

The difference is that S20 according to the second exemplary embodiment does not include S204, S30 does not include S303, S40 in a second exemplary embodiment is different from that in the first embodiment, and S50 does not include S502.

Specifically, as shown in FIG. 7A to FIG. 7D, the step of S40 in the second embodiment includes: S401, unlocking the locking mechanism 43, operating the upper end of the preset guide wire 30 to enable the preset guide wire 30 to ascend along the guiding catheter 81 until the lower end of the preset guide wire 30 is close to the distal opening of the inner branch 12 and positioned near the branch of the superior mesenteric artery C; S402, keeping the long sheath 71 immobile, operating the guiding catheter 81 to enable the distal end thereof to be close to the opening of the branch blood vessel, operating the upper end of the preset guide wire 30 to enable the lower end of the preset guide wire 30 to be selected into the superior mesenteric artery C; S403, keeping the long sheath 71 and the preset guide wire 30 immobile, and pushing the guiding catheter 81 downwards along the preset guide wire 30 to enable the distal end of the guiding catheter 81 to enter the superior mesenteric artery C; and S404, keeping the preset guide wire 30 and the guiding catheter 81 immobile, and pushing the long sheath 71 downwards to enable the lower end of the long sheath 71 to enter the superior mesenteric artery C along the guiding catheter 81.

S50 in a second embodiment is slightly different from S50 in the first exemplary embodiment in that no exchange of a delivery access guide wire is required in the second exemplary embodiment, i.e. S50 in the second exemplary embodiment does not include S501, and the delivery access guide wire used of the subsequent steps is replaced by preset guide wires.

The remaining steps are the same as those in the first exemplary embodiment and will not be depicted in detail herein.

It will be appreciated that in other embodiments, the delivery access guide wire may also be exchanged at S50 as in the first exemplary embodiment where the preset guide wire is withdrawn from the upper limb artery prior to exchanging a delivery access guide wire.

At S30 and S40 of the second exemplary embodiment, the preset guide wire is used as a vascular selection guide wire by directly utilizing the characteristics of the preset guide wire with double soft heads, thereby reducing the frequency of exchanging the guide wire, simplifying the steps of establishing a conveying path, and shortening the implantation time of the stent. Meanwhile, at S50, the preset guide wire can also be directly used as a delivery access guide wire of the delivery, further avoiding the implantation time extension caused by the exchange of guide wire.

Figure 8A:
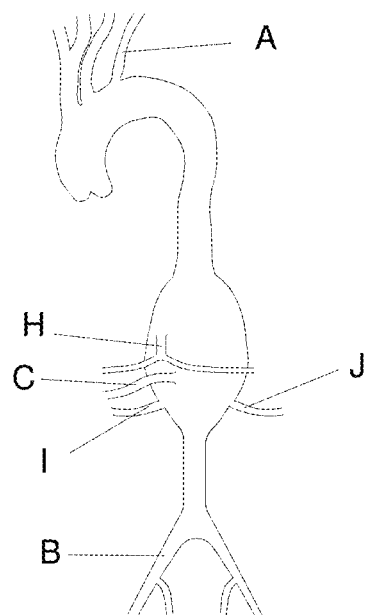
FIG. 8A is a schematic diagram showing the vascular structure of abdominal aortic aneurysm according to a third exemplary embodiment of the present application.
Figure 8B:
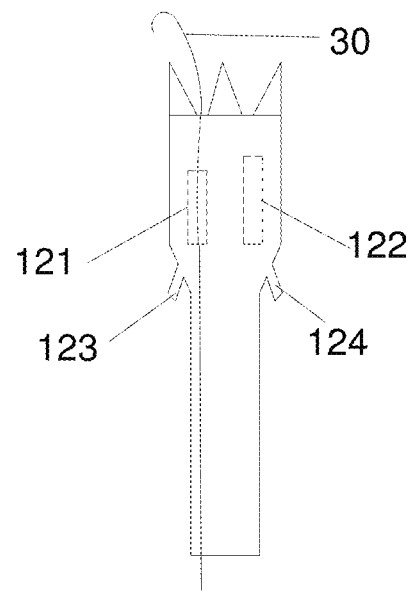
FIG. 8B is a schematic illustration of a main stent used for the vascular structure shown in FIG. 8A in accordance with the present application.

A third exemplary embodiment is primarily directed to the case where the thoracic abdominal aorta and a plurality of branch vessels are to be reconstructed. FIG. 8A shows schematically the structure of the corresponding blood vessels, including four branch vessels of the superior mesenteric artery C, the celiac trunk artery H, the right renal artery I and the left renal artery J. Accordingly, the corresponding main stent includes two inner branches 121 and 122, and two outer branches 123 and 124, and a preset guide wire 30 is correspondingly provided in only one inner branch 121, as shown in FIG. 8B.

The implantation method of the stent system in the third exemplary embodiment is substantially the same as the implantation method of the stent system in the second exemplary embodiment, except that after S503 it further includes S504 of withdrawing the preset guide wire 30 from the upper limb artery so as to enable the lower end of the preset guide wire 30 to enter the inner cavity of the main stent and be close to the proximal opening of the other inner branch; and that S60 is also included after S50.

Figure 8C:
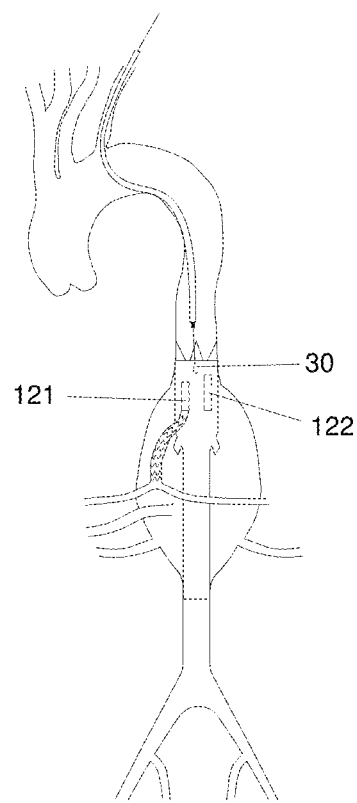
FIG. 8C is a schematic diagram outlining partial process of an implantation method of a stent system according to a third exemplary embodiment of the present application.

Specifically, S504 is performed after S503, by operating the upper end of the preset guide wire 30 to withdraw the preset guide wire 30 toward the left clavicular artery A until the lower end of the preset guide wire 30 enters the inner cavity of the main stent and is close to the proximal opening of the other inner branch 122 and then keeping the preset guide wire 30 immobile, as shown in FIG. 8C. The following step S50, the same as that in the second exemplary embodiment 2, is continued.

After S50, S60 is included by withdrawing the branch stent delivery through the upper limb artery, operating the upper end of the preset guide wire 30, pushing the preset guide wire 30 downwards to enable the lower end of the preset guide wire 30 to be selected into another branch blood vessel, and repeating the steps of S40 and S50.

It will be appreciated that when there are more than two inner branches on the main stent, S60 may be followed by S70, and S60 may be repeated to complete the implantation of all branch stents.

Figure 8D:
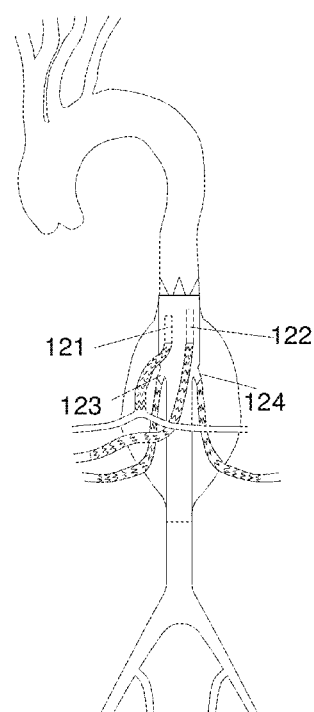
FIG. 8D is a schematic diagram outlining partial process of an implantation method of a stent system according to a third exemplary embodiment of the present application.
Figure 9A:
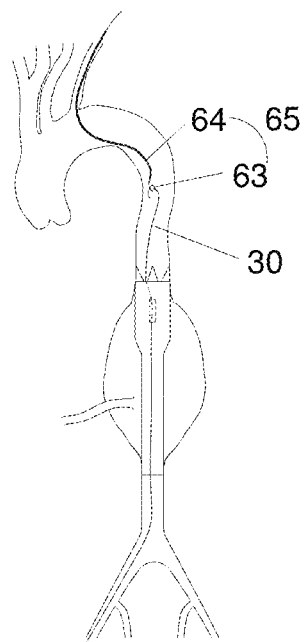
FIG. 9A is a schematic diagram outlining an implantation method of a stent system according to a fourth exemplary embodiment of the present application.
Figure 9B:
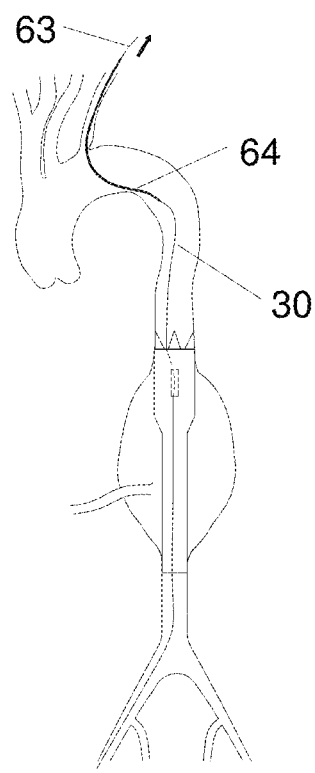
FIG. 9B is a schematic diagram outlining an implantation method of a stent system according to a fourth exemplary embodiment of the present application.
Figure 9C:
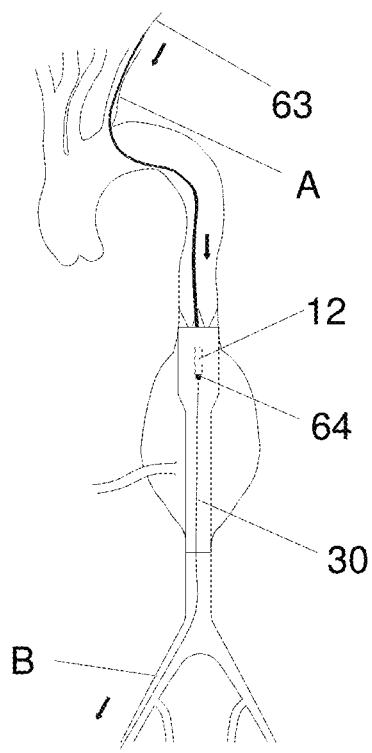
FIG. 9C is a schematic diagram outlining an implantation method of a stent system according to a fourth exemplary embodiment of the present application.
Figure 9D:
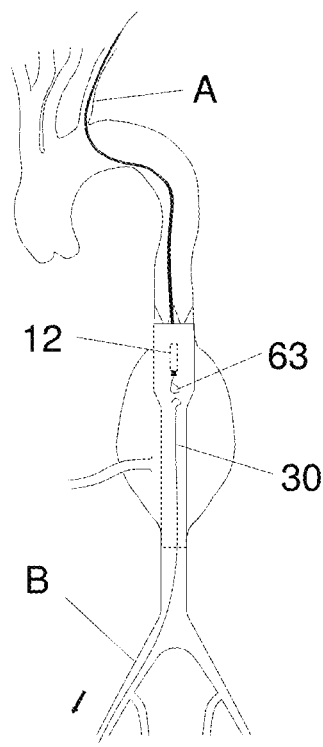
FIG. 9D is a schematic diagram outlining an implantation method of a stent system according to a fourth exemplary embodiment of the present application.
Figure 9E:
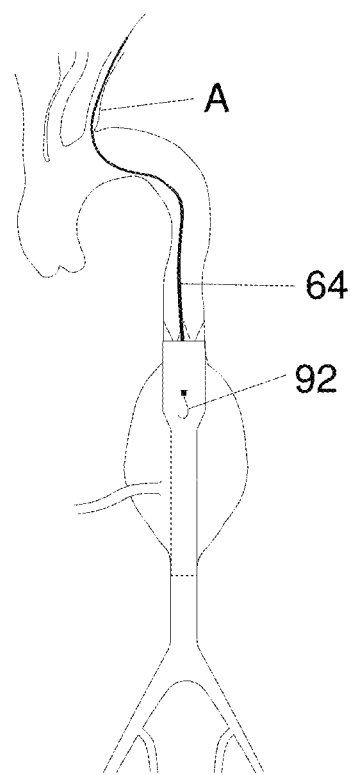
FIG. 9E is a schematic diagram outlining an implantation method of a stent system according to a fourth exemplary embodiment of the present application.
Figure 9F:
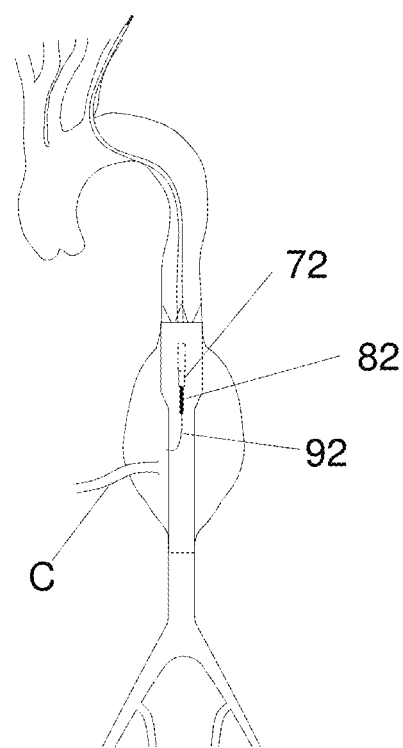
FIG. 9F is a schematic diagram outlining an implantation method of a stent system according to a fourth exemplary embodiment of the present application.

Understanding that in other embodiments, a preset guide wire may be provided in each inner branch in a plurality of stents, such that the preset guide wire in the corresponding inner branch may be completely withdrawn after the implantation of a branch stent. The implantation method of each branch stent is the same as that in the second exemplary embodiment. The final result of the stent system implantation is shown in FIG. 8D.

In the third exemplary embodiment, the number of branch stents can be implanted by using only one preset guide wire, thereby simplifying the structure of the stent system to avoid the plurality of preset guide wires entangling with each other to affect the implantation of the stent, and further reducing the exchange frequency of guide wires to greatly shorten the implantation time of the stent.

The implantation method of the stent system provided by a fourth exemplary embodiment includes the following steps of:

S80. implanting a main stent through a lower limb artery;

S90. introducing a catcher system through an upper limb artery, where the catcher system includes a catcher and a catcher catheter, and the catcher is used for catching the preset guide wire, and pulling down the preset guide wire from a femoral artery to enable the catcher catheter to extend out from the distal end of the inner branch along the preset guide wire;

S100. withdrawing the preset guide wire through the lower limb artery, introducing a vascular selection guide wire through the upper limb artery along the catcher catheter, withdrawing the catcher catheter, and introducing a long sheath and a guiding catheter through the upper limb artery along the vascular selection guide wire, where the long sheath and the guiding catheter are respectively provided with a proximal end and a distal end which are opposite, so as to make the distal end of the long sheath and the distal end of the guiding catheter extend out from the distal end of the inner branch; operating the vascular selection guide wire to enable the lower end of the vascular selection guide wire to enter a target branch blood vessel; operating the long sheath and the guiding catheter to enable the distal end of the long sheath and the distal end of the guiding catheter to enter the target branch blood vessel along the vascular selection guide wire;

S110. withdrawing the guiding catheter from the upper limb artery, and introducing a branch stent delivery along the long sheath through the upper limb artery to complete the implantation of the branch stent.

Also, S80 is the same as S10 in the first exemplary embodiment, and S110 is the same as S50 in the first exemplary embodiment, and therefore, no detail will not be depicted herein.

As shown in FIG. 9A to FIG. 9F, the step of S90 includes: S901, introducing the catching system 65 with the left clavicular artery A as an access path, where the catching system 65 includes a catcher catheter 64 and a catcher 63 crossing through the catcher catheter 64; S902, continuing to push the catcher system 65 towards the lower end to enable the distal end thereof to be close to the upper end of the preset guide wire 30, and operating the catcher system 65 to catch the preset guide wire 30; S903, withdrawing the catcher 63 to enable the upper end of the preset guide wire 30 to be received into the catcher catheter 64 together with the catcher 63; S904, pulling down the preset guide wire through the right femoral artery B, and meanwhile, pushing the catcher system 65 downwards at the left clavicular artery A to enable the lower end of the catcher catheter 64 to extend out of the distal opening of the inner branch 12 along the preset guide wire 30; S905, releasing the catcher, withdrawing the preset guide wire 30 through the right femoral artery B, and withdrawing the catcher 63 through the left clavicular artery A. S100 includes: S1001, withdrawing the preset guide wire 30 through the right femoral artery B, and introducing the preset guide wire 30 along the catcher catheter 64 through the left clavicular artery A; S1002, withdrawing the catcher catheter 64 through the left clavicular artery A, and introducing the long sheath 72 and the guiding catheter 82 along the vascular selection guide wire 90; S1003, operating the upper end of the vascular selection guide wire 92 to enable the lower end thereof to enter the superior mesenteric artery C, and operating the long sheath 72 and the guiding catheter 82 to enable the distal end of the long sheath 72 and the distal end of the guiding catheter 82 to sequentially enter the superior mesenteric artery C along the vascular selection guide wire 92.

The remaining operation steps are the same as those in the first exemplary embodiment and will not be depicted in detail herein.

At S90 in the fourth exemplary embodiment, the preset guide wire and the catcher system descend at the same time, so as to make the catcher catheter penetrate through the inner branch to facilitate the establishment of a subsequent delivering path of the branch stent, and the preset guide wire is withdrawn from the lower limb, thereby shortening the stent implantation time.

Understanding that the above detailed description of the embodiments account for only some implementation modes, and are not intended to suggest any limitation as to the present application. Person of ordinary skill in the art will be able to simply replace some of the operations according to practical requirements, and insubstantial changes may be made therein without departing from the spirit of the present application.

The invention claimed is:

1. An implantation method of a stent system, the stent system comprising a main stent, a branch stent and a preset guide wire, and the main stent comprises an inner branch through which the preset guide wire passes, wherein the implantation method of the stent system comprises:
implanting the main stent through a lower limb artery;
introducing a catcher system through an upper limb artery, and the catcher system comprises a catcher used for catching the preset guide wire, and withdrawing the catcher to enable the upper end of the preset guide wire to be exposed out of the upper limb artery;
introducing a long sheath and a guiding catheter along the preset guide wire through the upper limb artery, wherein the long sheath and the guiding catheter are respectively provided with a proximal end and a distal end which are opposite, so as to make the distal end of the long sheath and the distal end of the guiding catheter extend out from the distal end of the inner branch;
withdrawing the preset guide wire from the lower limb artery;
introducing a vascular selection guide wire along the guiding catheter through the upper limb artery, and operating the vascular selection guide wire to enable the lower end of the vascular selection guide wire to enter a target branch blood vessel;

operating the guiding catheter and the long sheath to enable the distal end of the long sheath and the distal end of the guiding catheter to enter the target branch blood vessel along the vascular selection guide wire; and withdrawing the guiding catheter from the upper limb artery and introducing a branch stent delivery through the upper limb artery along the long sheath to complete the implantation of the branch stent.

2. The implantation method of the stent system according to claim 1, wherein, before introducing the vascular selection guide wire and after withdrawing the preset guide wire, the method further comprises:

pushing the guiding catheter downwards to enable the distal end of the guiding catheter to be close to the opening of the target branch blood vessel.

3. The implantation method of the stent system according to claim 1, wherein before withdrawing the guiding catheter from the upper limb artery and after operating the guiding catheter and the long sheath to enable the distal end of the long sheath and the distal end of the guiding catheter to enter the target branch blood vessel along the vascular selection guide wire, the method further comprises:

withdrawing the vascular selection guide wire via the upper limb artery; and introducing a delivery access guide wire along the guiding catheter through the upper limb artery.

4. The implantation method of the stent system according to claim 1, wherein the step of introducing the long sheath and the guiding catheter along the vascular selection guide wire through the upper limb artery further comprises introducing the long sheath along the vascular selection guide wire and then introducing the guiding catheter along the vascular selection guide wire.

5. The implantation method of the stent system according to claim 1, wherein the step of operating the long sheath and the guiding catheter to enable the distal end of the long sheath and the distal end of the guiding catheter to enter the target branch blood vessel along the vascular selection guide wire further comprises operating the guiding catheter into the target branch blood vessel along the vascular selection guide wire and then operating the long sheath into the target branch blood vessel along the vascular selection guide wire.

6. An implantation method of a stent system, the stent system comprising a main stent, a branch stent and a preset guide wire, and the main stent comprises an inner branch through which the preset guide wire passes, wherein the implantation method of the stent system comprises:

implanting the main stent through a lower limb artery;

introducing a catcher system through an upper limb artery, and the catcher system comprises a catcher used for catching the preset guide wire, and withdrawing the catcher to enable the upper end of the preset guide wire to be exposed out of the upper limb artery;

introducing a long sheath and a guiding catheter along the preset guide wire through the upper limb artery, wherein the long sheath and the guiding catheter are respectively provided with a proximal end and a distal end which are opposite, so as to make the distal end of the long sheath and the distal end of the guiding catheter extend out from the distal end of the inner branch;

operating the upper end of the preset guide wire to enable the lower end of the preset guide wire to enter a target branch blood vessel;

operating the guiding catheter and the long sheath to enable the distal end of the long sheath and the distal end of the guiding catheter to enter the target branch blood vessel along the preset guide wire; and withdrawing the guiding catheter through the upper limb artery, and introducing a branch stent delivery along the long sheath through the upper limb artery to complete the implantation of the branch stent.

7. The implantation method of the stent system according to claim 6, wherein, before operating the upper end of the preset guide wire to enable the lower end of the preset guide wire to enter the target branch blood vessel and after the distal end of the long sheath and the distal end of the guiding catheter protrude from the distal end of the inner branch, the method further comprises:

withdrawing the preset guide wire through the upper limb artery to enable the lower end of the preset guide wire to be close to the distal opening of the inner branch.

8. The implantation method of the stent system according to claim 7, wherein, after withdrawing the preset guide wire from the upper limb artery to enable the lower end of the preset guide wire to be close to the distal opening of the inner branch and before operating the upper end of the preset guide wire to enable the lower end of the preset guide wire to enter the target branch blood vessel, the method further comprises:

operating the guiding catheter to enable the distal end of the guiding catheter to be close to the opening of the target branch blood vessel.

9. The implantation method of the stent system according to claim 6, wherein, before withdrawing the guiding catheter from the upper limb artery and introducing the branch stent delivery through the upper limb artery along the long sheath, and after guiding the distal end of the long sheath and the distal end of the guiding catheter into the target branch blood vessel along the preset guide wire, the method further comprises:

withdrawing the preset guide wire through the upper limb artery and introducing a delivery access guide wire along the guiding catheter.

10. The implantation method of the stent system according to claim 6, wherein, after introducing the branch stent delivery along the long sheath through the upper limb artery to complete the implantation of the branch stent, the method further comprises:

withdrawing the preset guide wire through the upper limb artery, so as to make the lower end of the preset guide wire enter the inner cavity of the main stent and close to the proximal opening of another inner branch.

11. The implantation method of the stent system according to claim 10, wherein after withdrawing the preset guide wire through the upper limb artery to make the lower end of the preset guide wire enter the inner cavity of the main stent and close to the proximal opening of the other inner branch, the method further comprises:

withdrawing the branch stent delivery through the upper limb artery, withdrawing the long sheath to enable the long sheath to enter the inner cavity of the main stent, and operating the upper end of the preset guide wire to enable the lower end of the preset guide wire to enter another target branch blood vessel.

12. The implantation method of the stent system according to claim 11, wherein, after withdrawing the branch stent delivery, operating the upper end of the preset guide wire to enable the lower end of the preset guide wire to enter another target branch blood vessel, the method further comprises:
- introducing the guiding catheter along the preset guide wire through the upper limb artery;
- operating the guiding catheter and the long sheath to enable the distal end of the guiding catheter and the distal end of the long sheath to enter the target branch blood vessel; and
- withdrawing the guiding catheter from the upper limb artery and guiding a branch stent delivery through the upper limb artery along the long sheath to complete the implantation of another branch stent.

13. The implantation method of the stent system according to claim 6, wherein, before completing the implantation of the branch stent, and after introducing the branch stent delivery, the method further comprises
- withdrawing the long sheath through the upper limb artery to enable the branch stent to be attached to the blood vessel wall after being released.

14. The implantation method of the stent system according to claim 6, wherein the preset guide wire comprises two tips and a body connecting the two tips, the two tips being less rigid than the body.

15. The implantation method of the stent system according to claim 6, wherein the preset guide wire is entered into the main stent through the distal opening of the inner branch.

16. An implantation method of a stent system, the stent system comprising a main stent, a branch stent and a preset guide wire, and the main stent comprises an inner branch through which the preset guide wire penetrates, wherein the implantation method of the stent system comprises:
- implanting the main stent through a lower limb artery;
- introducing a catcher system through an upper limb artery, and the catcher system comprises a catcher and a catcher catheter, and the catcher is used for catching the preset guide wire and pulling down the preset guide wire through a femoral artery, and pushing the catcher system downwards to enable the lower end of the catcher catheter to extend out from the distal end of the inner branch along the preset guide wire;
- withdrawing the preset guide wire through the lower limb artery, and introducing a vascular selection guide wire through the upper limb artery along the catcher catheter;
- withdrawing the catcher catheter, introducing a long sheath and a guiding catheter along the vascular selection guide wire through the upper limb artery, wherein the long sheath and the guiding catheter are respectively provided with a proximal end and a distal end which are opposite, so as to make the distal end of the long sheath and the distal end of the guiding catheter extend out from the distal end of the inner branch;
- operating the vascular selection guide wire to enable the lower end of the vascular selection guide wire to enter a target branch blood vessel;
- operating the long sheath and the guiding catheter to enable the distal end of the long sheath and the distal end of the guiding catheter to enter the target branch blood vessel along the vascular selection guide wire; and
- withdrawing the guiding catheter from the upper limb artery and introducing a branch stent delivery through the upper limb artery along the long sheath to complete the implantation of the branch stent.

17. The implantation method of the stent system according to claim 16, wherein, before operating the vascular selection guide wire to enable the lower end of the vascular selection guide wire to enter into the target branch blood vessel and after the distal end of the long sheath and the distal end of the guiding catheter extend out from the distal end of the inner branch, the method further comprises:
- pushing the guiding catheter downwards to enable the distal end of the guiding catheter to be close to the opening of the target branch blood vessel.

18. The implantation method of the stent system according to claim 16, wherein, before withdrawing the guiding catheter from the upper limb artery, and after the distal end of the long sheath and the distal end of the guiding catheter enter into the target branch blood vessel, the method further comprises:
- withdrawing the vascular selection guide wire through the upper limb artery; and
- introducing a delivery access guide wire along the guiding catheter through the upper limb artery.

* * * * *